United States Patent [19]

Faryniarz et al.

[11] Patent Number: 5,429,815
[45] Date of Patent: Jul. 4, 1995

[54] STABLE SINGLE-PHASE SELF-FOAMING CLEANSER

[75] Inventors: Joseph R. Faryniarz, Oxford; Anthony Patti, Trumbull; Amy C. Zimmerman, Ansonia, all of Conn.

[73] Assignee: Chesebrough-Pond's USA Co., Division of Conopco, Inc., Greenwich, Conn.

[21] Appl. No.: 226,181

[22] Filed: Apr. 11, 1994

[51] Int. Cl.⁶ .................................. A61K 7/00
[52] U.S. Cl. ........................ 424/47; 424/401; 252/90; 252/174.17; 252/DIG. 5; 514/844
[58] Field of Search .............. 252/90, 174.17, 174.21, 252/174.22, DIG. 5; 424/47, 401; 514/844, 846, 847

[56] References Cited

U.S. PATENT DOCUMENTS

| | | | |
|---|---|---|---|
| 4,595,522 | 6/1986 | Bartlett et al. | 252/305 |
| 5,002,680 | 3/1991 | Schmidt et al. | 252/90 |
| 5,160,739 | 11/1992 | Kanga | 424/401 |

Primary Examiner—Paul Lieberman
Assistant Examiner—Lorna M. Douyon
Attorney, Agent, or Firm—Milton L. Honig

[57] ABSTRACT

A sprayable cosmetic product is provided packaged in a clear bottle capable of withstanding at least 5 psig pressure fitted with a spray nozzle. The cosmetic composition contained therein is a clear, single-phase fluid containing a dialkyl ether/hydrocarbon as propellant system and a concentrate which requires a surfactant and optimally may contain a coupling agent. When present, the coupling agent is a propoxylated adduct of mono or polyhydric alcohols. Upon activation of the spray nozzle, a thick, creamy mousse is expressed. These compositions will preferably have a pH ranging from about 3.0 to 6.5.

13 Claims, No Drawings

STABLE SINGLE-PHASE SELF-FOAMING CLEANSER

BACKGROUND OF THE INVENTION

1. Field of the Invention

The invention concerns a cosmetic cleanser, especially for application to the face.

2. The Related Art

Properly formulated cleansers will effectively and efficiently remove previously applied face powder, rouge, foundation bases, eyeshadow and lipstick. Commercial facial cleansers depend on surfactant ingredients. These surfactants, when contacted with water, sometimes generate a bubbly foam. The cleansers of commerce are usually found in either a gel, lotion or cream form. There is, however, a continual search for less traditional forms that would provide an aesthetically pleasing presentation.

There was recently disclosed in U.S. Pat. No. 5,002,680 (Schmidt et al) a skin-cleansing mousse comprising an aerosol dispenser containing an emulsion formed from a concentrate and 3 to 12% by weight of a propellant. The concentrate requires an anionic or amphoteric surfactant, e.g. lauramido/myristamidopropyl betaine or a lauryl sarcosinate, a cationic polymer and an occlusive or nonocclusive moisturizer. These formulas are not believed to be single phase. Invariably, the concentrate-propellant compositions leading to mousses are packaged in opaque, pressure-resistant, metal cans. Aesthetic visual focus of mousse products is generally on the resulting creamy foam rather than the delivery system or concentrate upon which they depend.

In a co-pending application (Zimmerman et al. Ser. No. 08/110,275) is described a sprayable cosmetic product packaged in a clear bottle capable of withstanding pressure and fitted with a spray nozzle. Within the bottle is a clear, single phase cosmetic composition containing a hydrocarbon propellant and a concentrate containing α-olefin sulphonate salts, alkyl polyglucosides and betaines. This cosmetic composition is only borderline phase stable and in its manufacture requires either mechanical or ultrasound agitation to disperse propellant into the concentrate phase. Special costs are therefore involved not only in the extra processing but also in the cost of added capital equipment.

Accordingly, it is an object of the present invention to provide a new format for delivery of a skin cleanser.

it is another object of the present invention to maintain an alcohol-free, single-phase liquid concentrate for a mousse format.

It is yet another object of the present invention to form the single-phase liquid concentrate with a propellant readily miscible therewithin without necessity for special agitation to achieve homogeniety.

It is still another object of the present invention to provide a single-phase liquid concentrate with propellant readily miscible therewithin to achieve a homogeneous system of improved phase stability.

It is still another object of the present invention to provide a single-phase liquid concentrate of improved clarity, substantially lower concentrate viscosity and better foam aesthetics.

These and other objects of the present invention will more readily become apparent from the description and examples which follow.

SUMMARY OF THE INVENTION

A sprayable cosmetic product is provided including:
(i) a clear bottle capable of withstanding at least 10 psig, the bottle including at an open mouth thereof a spray nozzle; and
(ii) a clear, single-phase cosmetic composition including:
   (a) from about 0.5 to about 20% of a mixture of a $C_1$-$C_6$ alkyl ether and a hydrocarbon propellant in a relative weight ratio ranging from about 10:1 to 1:10; and
   (b) from about 0.5 to about 40% of at least one surfactant in an aqueous medium;
wherein upon actuation of the spray nozzle, a creamy foam mousse is expressed from the bottle.

Advantageously, the cosmetic composition can include a coupling agent in an amount from about 0.5 to about 20% by weight. The coupling agent may be propylene glycol or a propoxylated adduct of a $C_1$-$C_{20}$ mono or polyhydric alcohol. Most effective is the propoxylated adduct of formula:

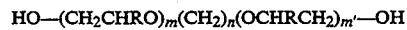

wherein m and m' are integers greater than 1, and n is an integer greater than 3; and R is selected from the group consisting of hydrogen, $C_1$-$C_{12}$ alkyl and mixtures thereof.

In another aspect of the present invention there is provided a sprayable cosmetic composition including:
(a) from about 0.5 to about 20% of a mixture of a $C_1$-$C_6$ alkyl ether and a hydrocarbon propellant in a relative weight ratio ranging from about 10:1 to 1:10; and
(b) from about 0.5 to about 40% of at least one surfactant in an aqueous medium,
wherein a creamy foam mousse results upon spraying of the composition through a spray nozzle.

Preferably the composition will also contain from about 0.5 to about 20% of a coupling agent having formula:

Of special effectiveness as the surfactant are the alkyl polyglucosides. Most preferred as the coupling agent is PPG-10 butanediol.

DETAILED DESCRIPTION OF THE INVENTION

Now there has been developed a concentrate-propellant system for a self-foaming cleanser that achieves increased miscellization and solubilization of propellant within the aqueous fluid of the system. Propellant is easily blended without the formerly required vigorous mechanical agitation. Good foaming is achieved that does not significantly change as more of the product has discharged. The ordinarily high viscosity of the concentrate is reduced to an easily sprayable fluid. Moreover, the system provides significant vapor pressure reduction thereby increasing safety against any accidental rupture of the dispenser package. More specifically, there is provided a clear, single phase liquid cosmetic composition containing at least one surfactant and a special mixture of propellant gases.

According to the invention a first essential component of the cosmetic composition is a mixture of a $C_1$–$C_6$ alkyl ether and a $C_3$–$C_6$ hydrocarbon propellant. Suitable hydrocarbons are n-butane known as A17, isobutane known as A31, isobutane/propane mixture available as A46 and combinations thereof. Suitable $C_1$–$C_6$ alkyl ethers include dimethyl ether, diethyl ether, methylethyl ether and diisopropyl ether. Most preferred is dimethyl ether.

Alkyl ether to hydrocarbon propellant will range in weight from about 10:1 to 1:10, preferably from 2:1 to 1:2, optimally about 1:1. Total concentration of propellants will range from about 1 to about 15%, preferably from about 2 to about 10%, optimally between about 3 and 4% by weight.

Surfactants will also be present in the cosmetic compositions of the present invention. Total concentration of the surfactant will range from about 0.5 to about 40%, preferably from about 7 to about 35%, optimally from about 20 to no higher than 30% by weight of the total cosmetic composition. Each individual surfactant may be present in an amount from about 0.5 to about 20%, preferably no higher than about 10% by weight. The surfactant may be selected from the group consisting of anionic, cationic, nonionic and amphoteric actives. Especially useful is a combination of an anionic and an amphoteric surfactant in a relative weight ratio from about 5:1 to 1:5, preferably from about 3:1 to 1:3, optimally about 1:1. Even more preferred is the further addition of a nonionic surfactant such that the ratio of total anionic and amphoteric to nonionic surfactant ranges from about 10:1 to 1:10, preferably from about 5:1 to 1:1, optimally from about 4:1 to 2:1 by weight.

When the concentrate is held at a pH of no higher than 5.0, it is advantageous to employ a $C_8$–$C_{30}$ $\alpha$-olefin sulphonate salt as the anionic surfactant. Salt cations to be used with the sulphonate may be selected from alkali metals, ammonium and $C_1$–$C_{20}$ alkanolammonium ions. In general, it is advantageous that the anionic surfactants of the present invention all exhibit an HLB of at least 15.

Representative of the amphoteric surfactant category are the $C_8$–$C_{30}$ amine oxides and betaines. Illustrative of the latter type are the $C_8$–$C_{30}$ fatty alkyl amido betaines, sulphobetaines and mixtures thereof. Most preferred is cocoamidopropyl betaine.

Advantageously, the concentrate will also contain a nonionic surfactant, especially a $C_6$–$C_{20}$ alkyl polyglucoside, an example of which is Plantareen 2000® available from the Henkel Corporation of Ambler, Pa. Polyglucosides assist the anionic surfactant to solubilize the propellant and significantly improve mildness of the cosmetic composition.

Coupling agents may also be included and can provide an extra measure of assistance for compatiblizing propellants with the concentrate so as to obviate need for any mechanical agitation to form a single-phase composition. The coupling agent may be propylene glycol or a propoxylated adduct of a $C_1$–$C_{20}$ mono or polyhydric alcohol. Propoxylated sugars such as Glucam P-10 (a 10 mole propoxylated glucose ester) is a suitable coupler. Most preferred, however, as the coupling agent will be structures having the formula:

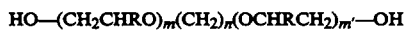

wherein m and m' are integers ranging anywhere from 2 to 100, preferably from 3 to 20, optimally between 4 and 8; n is an integer ranging from 4 to 20, preferably between 4 and 10, optimally from 4 to 6; and R is selected from the group consisting of methyl and hydrogen.

The coupling agent, as in the above formula, may be seen as formed from the alkoxylation of a $C_4$–$C_{20}$ alkylene diol. Ethylene oxide and propylene oxide are the preferred alkoxylating units. Preferred diols are 1,4-butanediol, 1,5-pentanediol, 1,6-hexanediol and 1,12-dodecanediol. A particularly preferred coupling agent is PPG-10 butanediol (CTFA nomenclature) available from PPG-Mazer Chemicals Inc. under the trademark Macol 57 or from Croda, Inc. under the trademark ProButyl DB10.

Concentrates of the present invention will include water as the major component. Water will range in an amount from about 30 to about 98%, preferably from about 45 to about 95%, optimally from about 50 to 75% by weight of the total cosmetic composition.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerol. The amount of humectant may range anywhere from 0.5 to 20%, preferably between 1 and 15% by weight of the composition.

With certain combinations of component materials, the cosmetic compositions of the present invention may also include a $C_1$–$C_4$ monohydric alcohol. Levels of the monohydric alcohol may range from about 1 to about 40% by weight of the composition. Preferably, however, the compositions should be essentially free of monohydric alcohols such as ethanol. In tests evaluating certain of the cosmetic compositions, the presence of ethanol suppressed the fragrance emitted upon formation of mousse as this was being generated from the spray nozzle.

Compositions of the present invention may also contain $C_1$–$C_{20}$ $\alpha$-hydroxycarboxylic acids and salts thereof. The salts are preferably alkalimetal, ammonium and $C_1$–$C_{12}$ alkanolammonium salts. Illustrative acids are glycolic acid, lactic acid and 2-hydroxycaprylic acid. Most preferred is a combination of glycolic and 2-hydroxycaprylic acids and their ammonium salts. Levels of these materials may range from about 0.01 to about 15%, preferably from about 0.05 to about 8%, optimally between about 0.1 and 1% by weight of the cosmetic composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, propyl paraben, imidazolidinyl urea, sodium dehydroacetate, and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Compounds that can provide α-hydroxyacids upon hydrolysis may also be useful as components of the cosmetic composition. In particular, $C_8$–$C_{30}$ acyl lactylate and salts thereof may be employed. The alkalimetal, ammonium and $C_1$–$C_{12}$ alkanolammonium salts are most effective. A preferred example is $C_{12}$–$C_{14}$ acyl lactylate, commercially available as Pationic 138 from the RITA Corporation. Amount of the lactylate may range from about 0.1 to about 10%, preferably from about 0.2 to about 3%, optimally between about 0.5 and 1.5% by weight of the cosmetic composition.

When compositions of the present invention include as surfacant a mixture of α-olefin sulphonate salt and alkyl polyglucoside, the ratio will be about 10:1 to 1:10, preferably 3:1 to 1:3, optimally between about 2:1 to 1:1 by weight.

Minor adjunct ingredients may also be present in the cosmetic compositions. These ingredients include vitamins (such as vitamin E acetate, vitamin A palmitate and DL-panthenol), fragrances and thickeners. Levels of fragrance may range from about 0.05 to about 5%, preferably between 0.1 and 1% by weight.

Compositions of the present invention will preferably be contained in a clear bottle pressurizable to the extent that the bottle can withstand at least 5 psig, preferably at least from 25 to 50 psig pressure. Suitable for this purpose is a glass bottle sold by the Wheaton Glass Company, Model M937F. The preferred embodiment will include a clear, plastic coating (0.01 to 0.1 inches thick), such as polyvinyl chloride (preferred mode), polyolefin, polyacrylate or polyurethane, fully surrounding an exterior surface of the glass bottle. A standard aerosol spray nozzle will be fitted within a mouth of the bottle, normally crimped therewithin to establish a pressure resistant seal.

concentrate in an amount from about 80 to about 99.5%, preferably from about 87 to about 97% by weight, and a propellant in an amount from about 0.5 to 10%, preferably from about 1 to about 6%, optimally about 3 to 5% by weight.

The term "clear" is intended to be synonymous with transparent. More technically this is defined as a material having a maximum transmittance of light of at least 4% of any wavelength in the range of 200 to 800 nm through a sample 10 cm thick. A clear or transparent composition or glass is one which also permits sufficient light transmittance to enable reading of newspaper print through a thickness commensurate with the diameter of a bottle pursuant to the claimed invention.

Colorants will also be incorporated as minor ingredients into the cosmetic composition. By the term colorants is meant any water-soluble dye which imparts a color in the visible range to that of the composition. Colors may include red, yellow, blue and green as well as shades therebetween. Most preferred, however, are the red or pink dyes. Illustrative of this category are FD&C Red No. 3, Red No. 4, Red No. 40 and the D&C colorants Red No. 6, Red No. 28 and Red No. 33. Most preferred is Red No. 33. Active levels of this material may range from about 0.001 to about 1%, preferably between about 0.01 and about 0.1% by weight.

The following Examples will more fully illustrate the embodiments of this invention. All parts, percentages and proportions referred to herein and in the appended claims are by weight unless otherwise indicated.

EXAMPLE 1

A series of concentrates are listed in Table I which illustrate typical formulations of the present invention. These concentrates are then combined with a 1:1 mixture of dimethyl ether and hydrocarbon propellant. Concentrate and propellant form a single phase transparent liquid. The resulting cosmetic compositions are then packaged into a Wheaton Model 937F pressure-resistant glass bottle. A spray nozzle head is then inserted into the mouth of the bottle and crimped around the mouth to achieve a pressure seal.

TABLE I

| TRADEMARK | CTFA Nomenclature | WEIGHT %* | | | | | |
|---|---|---|---|---|---|---|---|
| | | 1 | 2 | 3 | 4 | 5 | 6 |
| — | Glycerin | 6.00 | 6.00 | 6.00 | 6.00 | 6.00 | 6.00 |
| Bioterge AS-40 | Sodium α-Olefin Sulfonate | 10.00 | 4.00 | 2.80 | 5.16 | 4.76 | 5.16 |
| Plantareen 2000 | $C_6$–$C_{12}$/$C_{10}$–$C_{16}$ Alkyl Polyglucoside | — | 2.80 | 1.98 | 1.70 | 3.30 | 1.70 |
| Tegobetaine C | Cocoamidopropyl Betaine | 10.00 | 3.30 | 3.30 | 3.30 | 3.30 | 3.30 |
| ProButyl DB10 | PPG-10 Butanediol | 5.00 | 5.00 | 5.00 | 8.00 | 3.00 | 10.00 |
| Pationic 138C | Sodium Lauroyl Lactylate | 0.50 | 0.50 | 0.50 | 0.50 | 0.50 | 0.50 |
| Glypure | Glycolic Acid | 0.36 | 0.36 | 0.36 | 0.36 | 0.36 | 0.36 |
| — | Ammonium Hydroxide | 0.13 | 0.13 | 0.13 | 0.13 | 0.13 | 0.13 |
| — | Fragrance | 0.16 | 0.16 | 0.16 | 0.16 | 0.16 | 0.16 |
| — | α-Hydroxycaprylic Acid | 0.05 | 0.05 | 0.05 | 0.05 | 0.05 | 0.05 |
| — | FD&C Red No. 33 | 0.03 | 0.03 | 0.03 | 0.03 | 0.03 | 0.03 |
| Glydant Plus | DMDM Hydantoin | 0.10 | 0.10 | 0.10 | 0.10 | 0.10 | 0.10 |
| Stabilizer 89 | Butyl Methoxydibenzoylmethane | 0.05 | 0.05 | 0.05 | — | 0.05 | 0.05 |
| — | Vitamin E Acetate | 0.05 | 0.05 | 0.05 | 0.05 | 0.05 | 0.05 |
| — | DL-Panthenol | 0.05 | 0.05 | 0.05 | 0.05 | 0.05 | 0.05 |
| — | Benzophenone-4 | — | — | — | 0.05 | — | — |
| — | SD40 Alcohol | — | — | — | — | — | 5.00 |
| — | Water | | | BALANCE | | | |

*Listed as % active

Compositions of the present invention will be a clear, single-phase cosmetic composition. The cosmetic composition will normally fill anywhere from 30 to 99% of the bottle capacity. This composition will include a All the foregoing Examples form clear fluid compositions and exhibit a pH between 4.7 and 4.9.

EXAMPLE 2

A series of experiments were conducted to evaluate the effectiveness of various materials as coupling agents. Each of these materials was tested within the context of the base formula appearing in Table II.

TABLE II

| COMPONENT | % CONCENTRATE |
| --- | --- |
| Tegobetaine C | 13.20 |
| Sodium C14–16 Olefin Sulfonate | 12.00 |
| Plantareen 2000 ® | 6.12 |
| Glycerine USP | 6.00 |
| Coupling Agent | 5.00 |
| Pationic 138C | 1.00 |
| Dipropylene Glycol Isoceteth-20 Acetate | 1.00 |
| Glycolic Acid | 0.36 |
| Methyl Paraben | 0.15 |
| Ammonium Hydroxide | 0.13 |
| EDTA Disodium Salt | 0.05 |
| DL Panthenol | 0.05 |
| Hydroxy Caprylic Acid | 0.05 |
| Benzophenone-4 | 0.05 |
| Fragrance | 0.03 |
| Deionized Water | Balance |

Table III lists the candidate materials for coupling agent and describes their effect upon the product. For these tests, the level of concentrate and propellant were 97 and 3%, respectively. The propellant was a mixture of dimethyl ether and A31 in a 40:60 weight ratio.

TABLE III

| COUPLING AGENT CANDIDATE | RESULTANT PROPERTIES OF CONCENTRATE/PROPELLANT SYSTEM | |
| --- | --- | --- |
| | Viscosity (cps) | Clarity |
| PPG-10 Butanediol | 8.0 | Clear Single-Phase |
| PPG-50 Cetyl Ether | 6.7 | Cloudy |
| PPG-50 Oleyl Ether | 8.0 | Cloudy |
| PPG-10 Cetyl Ether | 220 | Cloudy |
| PPG-3 Myristyl Ether | Gelled | Cloudy |

One of the requirements of the propellant system is to reduce the viscosity of the concentrate (210 cps). PPG-10 Cetyl Ether and PPG-3 Myristyl Ether both failed with respect to reducing viscosity of the product system. Low viscosity is required for sprayability. Although PPG-50 Cetyl Ether and PPG-50 Oleyl Ether provided an appropriate viscosity, the product system was never clear. Only PPG-10 Butanediol met the criteria of lowering viscosity and providing good clarity (indicative of coupling propellant with concentrate).

EXAMPLE 3

A series of experiments were done to consider the effects of propellant chemistry. Each of the product systems utilized the concentrate as outlined under Example 2.

TABLE IV

| | FORMULA (%) | | |
| --- | --- | --- | --- |
| | A | B | C |
| COMPONENT | | | |
| Concentrate (Ex. 2) | 97 | 97 | 94 |
| Dimethyl Ether | 3 | — | 3 |
| Hydrocarbon A46 | — | 3 | 3 |
| PERFORMANCE | | | |
| Pressure (psig) | 5 | 28 | 37 |
| Foam (75% Extrusion) | None | Poor | Good |

From the results in Table IV, it is evident that a combination of dimethyl ether and hydrocarbon performs much better than either propellant alone. For instance, A46 at 6% is not soluble in the concentrate but a propellant blend of 3% each of A46 and DME, as seen in Formula C, achieves solubility yet still foams well on extrusion through the spray nozzle.

EXAMPLE 4

A series of experiments were conducted to evaluate the potential of various materials as coupling agents. The base formula employed was essentially identical to that outlined under Example 2. In this instance, however, the propellant was only hydrocarbon, i.e. isobutane. Table V outlines the coupling agent candidates and their effect upon concentrate viscosity and single-phase formation.

TABLE V

| COUPLING AGENT CANDIDATE | VISCOSITY (cps) | SINGLE-PHASE FORMATION |
| --- | --- | --- |
| Dipropylene Glycol Isoceteth-20 Acetate | 300.0 | Good (at 1%) Poor (at 2%) |
| PPG-5 Ceteth-20 | gel | Good (above 1% gels) |
| PPG-15 Stearyl Ether | — | Good |
| PPG-10 Butane Diol | 9.0 | Excellent (0.5–10%) |
| Ethyl Alcohol | — | Good to Excellent (1–70%) |
| Methylal | 28.5 | Fair |
| Propylene Glycol Isoceteth-3 Acetate | — | Poor |
| Propylene Glycol Ceteth-3 Acetate | — | Poor |
| Sodium Chloride | — | Poor, not clear about 1% |
| Urea | — | Poor |
| Propylene Glycol | — | Fair, improves to Good at 10% |
| Sodium Xylene Sulfonate | 1.40 | Fair |
| Laureth-2 Benzoate | 316 | Poor |
| C-12–13 Alcohols | 52.0 | Poor |
| Dipropylene Glycol | 23.5 | Fair to Good at 10% |
| Butoxytriglycol | 8.0 | Fair |
| Butyldipropasol (butyl alcohol + 2 moles propylene oxide) | 19.5 | Fair |
| Dipropylene Glycol n-Butyl Ether | 20.0 | Fair |
| Dipropylene Glycol Methyl Ether | 14.5 | Fair |
| Triethyl Citrate | 12.5 | Poor |
| Polypropylene Glycol | 11.0 | Poor |
| POE-5 Ceteth 20 | 219 | Poor |
| Oleth-4 | gel | Poor |
| Polysorbate 20 | gel | Fair |

TABLE V-continued

| COUPLING AGENT CANDIDATE | VISCOSITY (cps) | SINGLE-PHASE FORMATION |
|---|---|---|
| C12-15 Alkyl Benzoate | 295 | Poor |

Only those materials which reduced the concentrate viscosity to less than 50 cps were acceptable. Concentration viscosities higher than this level were not easily sprayable. Evident from the table is that propoxylated adducts of mono and polyhydric alcohols perform the best as coupling agents.

EXAMPLE 5

A series of experiments were conducted to evaluate the effect of differences in the ratio of ether to hydrocarbon propellants on foam quality and single-phase homogeneity. Effects of the different propellant ratios were conducted on the composition of Example 2 (Table II; coupling agent=PPG-10 butanediol) (hereinafter known as Formula III) and Formula I and II outlined under Table VI.

TABLE VI

| COMPONENT | % CONCENTRATE FORMULA I | FORMULA II |
|---|---|---|
| Plantaren 2000 ® | 30.00 | 26.00 |
| Tegobetaine C ® | — | 10.00 |
| Glucam P-10 ® | 6.00 | 6.00 |
| Dipropylene Glycol Isoceteth-20 Acetate | 1.00 | 1.00 |
| Pationic 138C ® | 0.80 | 0.80 |
| Polymer JR ® | 0.50 | 0.50 |
| Glycolic Acid 70% | 0.36 | 0.36 |
| Fragrance | 0.16 | 0.16 |
| Methylparaben NF | 0.15 | 0.15 |
| Ammonia, AQUA 26BE | 0.13 | 0.13 |
| Disodium EDTA | 0.05 | 0.05 |
| Benzophenone-4 | 0.05 | 0.05 |
| Vitamin E Acetate | 0.05 | 0.05 |
| DL-Panthenol | 0.05 | 0.05 |
| Hydroxycaprylic Acid | 0.05 | 0.05 |
| Colorant | 0.03 | 0.03 |
| Deionized Water | qs | qs |

Total propellant concentrations of 3 and 6% were utilized for the comparative tests. Table VII lists the propellant code identifying the specific ratio of dimethyl ether to isobutane.

TABLE VII

| PROPELLANT CODE | % DME | % A-31 |
|---|---|---|
| A | 10 | 90 |
| B | 20 | 80 |
| C | 30 | 70 |
| D | 40 | 60 |

Evaluation of how much propellant was solubilized was determined through the following procedures. When propellants were first gassed into the test bottles it was noted whether or not a layer formed. The "Ten Turn Test" was then applied. This test simply involved gently turning each bottle, end over end, for ten times. Table VIII reports the results of these compatibility evaluations.

TABLE VIII

| DME/A31 FILL | A 3% | A 6% | B 3% | B 6% | C 3% | C 6% | D 3% | D 6% |
|---|---|---|---|---|---|---|---|---|
| FORMULA I | | | | | | | | |
| TT | NC | NC | NC | NC | TT | TT | TT | NC |
| 5SEC | CLR | NC | CLR | NC | CLR | NC | CLR | CLR |
| F5S | NG | | NG | | NG | | NG | OK |
| FS | NG | | OK | | OK | | OK | OK |
| FORMULA II | | | | | | | | |
| TT | NC | NC | NC | NC | NC | NC | TT | NC |
| 5SEC | CLR | NC | CLR | NC | CLR | CLR | CLR | CLR |
| F5S | NG | | NG | | NG | OK | NG | OK |
| FS | NG | | OK | | OK | OK | OK | OK |
| FORMULA III | | | | | | | | |
| TT | NC | NC | NC | NC | NC | NC | NC | NC |
| 5SEC | NC | NC | NC | NC | NC | NC | CLR | CLR |
| F5S | | | | | | | NG | NG |
| FS | | | | | | | OK | OK |

LEGEND:
F5S = FOAM QUALITY AFTER 5 SECONDS OF SHAKING AND SITTING STILL OVERNIGHT
FS = FOAM QUALITY SHAKEN AS PER CUSTOMER DIRECTIONS
NC = NOT CLEAR AFTER 5 SECONDS OF SHAKING
CLR = PRODUCT WAS CLEAR AFTER 5 SECONDS OF SHAKING
TT = PRODUCT WAS CLEAR AFTER TEN TURN TEST
NG - FOAM QUALITY NOT GOOD
OK = ACCEPTABLE FOAM QUALITY

Employment of dimethyl ether is seen to assist the solubilization of isobutane into solution. Best results were obtained with 30:70 and 40:60 ratios of dimethyl ether to isobutane.

Although this invention has been described with reference to specific Examples, it will be apparent to one skilled in the art that various modifications will be suggested, all of which are within the spirit and purview of this invention.

What is claimed is:

1. A sprayable cosmetic product comprising:
   (i) a clear bottle capable of withstanding at least 10 psig, the bottle including at an open mouth thereof a spray nozzle; and
   (ii) a clear, single-phase cosmetic composition comprising:
      (a) from about 0.5 to about 20% by weight of a propellant mixture consisting of a $C_1$–$C_6$ alkyl ether and a $C_3$–$C_6$ unsubstituted hydrocarbon propellant in a relative weight ratio ranging from about 10:1 to 1:10;
      (b) from about 0.5 to about 40% by weight of at least one surfactant in an aqueous medium; and
      (c) from about 0.5 to about 20% by weight of a coupling agent having formula:

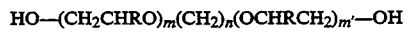

$$\mathrm{HO-(CH_2CHRO)}_m\mathrm{(CH_2)}_n\mathrm{(OCHRCH_2)}_{m'}\mathrm{-OH}$$

wherein m and m' are integers greater than 1, and n is an integer greater than 3; and R is selected from the group consisting of hydrogen, $C_1$–$C_{12}$ alkyl and mixtures thereof;
wherein upon actuation of the spray nozzle, a creamy foam mousse is expressed from the bottle.

2. A cosmetic product according to claim 1 wherein the bottle is formed of glass.

3. A cosmetic product according to claim 1 wherein the $C_1$–$C_6$ alkyl ether is dimethyl ether.

4. A cosmetic product according to claim 3 wherein the dimethyl ether and hydrocarbon propellant are present in a weight ratio from about 2:1 to about 1:2.

5. A cosmetic product according to claim 1 wherein the coupling agent is PPG-10 butanediol.

6. A cosmetic product according to claim 1 wherein the surfactant is a $C_6$–$C_{20}$ alkyl polyglucoside.

7. A cosmetic product according to claim 1 wherein the composition has a pH ranging between about 3.0 and 6.5.

8. A cosmetic composition comprising:
(a) from about 0.5 to about 20% by weight of a propellant mixture consisting of a $C_1$–$C_6$ alkyl ether and a $C_3$–$C_6$ unsubstituted hydrocarbon propellant in a relative weight ratio ranging from about 10:1 to 1:10;
(b) from about 0.5 to about 40% by weight of at least one surfactant in an aqueous medium; and
(c) from about 0.5 to about 20% by weight of a coupling agent having formula:

$$HO-(CH_2CHRO)_m(CH_2)_n(OCHRCH_2)_{m'}-OH$$

wherein m and m' are integers greater than 1, and n is an integer greater than 3; and R is selected from the group consisting of hydrogen, $C_1$–$C_{12}$ alkyl and mixtures thereof:
wherein a creamy foam mousse results upon spraying of the composition through a spray nozzle.

9. A cosmetic composition according to claim 8 wherein the $C_1$–$C_6$ alkyl ether is dimethyl ether.

10. A cosmetic composition according to claim 9 wherein the dimethyl ether and hydrocarbon propellant are present in a weight ratio from about 2:1 to about 1:2.

11. A cosmetic composition according to claim 8 wherein the coupling agent is PPG-10 butanediol.

12. A cosmetic composition according to claim 8 wherein the surfactant is a $C_6$–$C_{20}$ alkyl polyglucoside.

13. A cosmetic composition according to claim 8 wherein the composition has a pH ranging between about 3.0 and 6.5.

* * * * *